US012611374B2

(12) United States Patent
Segarra Lopez et al.

(10) Patent No.: US 12,611,374 B2
(45) Date of Patent: Apr. 28, 2026

(54) DERMATOLOGICAL COLLAR FOR NON-HUMAN ANIMALS

(71) Applicant: Bioiberica, S.A.U., Barcelona (ES)

(72) Inventors: Sergi Segarra Lopez, Barcelona (ES); Elena Ramos Motilva, Barcelona (ES); Jaume Girbent Fernandez, Girona (ES); Alfonso Velasco Franco, Barcelona (ES); Arnaud Vilbert, Baziege (FR); Sophie Leclerc, Escalquens (FR)

(73) Assignee: Bioiberica, S.A.U., Barcelona (ES)

( * ) Notice: Subject to any disclaimer, the term of this patent is extended or adjusted under 35 U.S.C. 154(b) by 363 days.

(21) Appl. No.: 17/690,520

(22) Filed: Mar. 9, 2022

(65) Prior Publication Data

US 2023/0044738 A1 Feb. 9, 2023

(30) Foreign Application Priority Data

Jul. 30, 2021 (EP) .................................... 21382717

(51) Int. Cl.

| | |
|---|---|
| A61K 9/00 | (2006.01) |
| A01K 27/00 | (2006.01) |
| A61K 31/164 | (2006.01) |
| A61K 31/232 | (2006.01) |
| A61K 31/685 | (2006.01) |
| A61K 31/688 | (2006.01) |
| A61K 31/7032 | (2006.01) |
| A61K 31/7034 | (2006.01) |
| A61K 47/34 | (2017.01) |
| A61P 17/00 | (2006.01) |
| A61P 17/04 | (2006.01) |
| C08L 75/04 | (2006.01) |

(52) U.S. Cl.
CPC .......... *A61K 9/0017* (2013.01); *A01K 27/001* (2013.01); *A01K 27/007* (2013.01); *A61K 31/164* (2013.01); *A61K 31/232* (2013.01); *A61K 31/685* (2013.01); *A61K 31/688* (2013.01); *A61K 31/7032* (2013.01); *A61K 31/7034* (2013.01); *A61K 47/34* (2013.01); *A61P 17/00* (2018.01); *A61P 17/04* (2018.01); *C08L 75/04* (2013.01); *C08L 2203/02* (2013.01)

(58) Field of Classification Search
CPC .. A61K 9/0017; A61K 31/164; A61K 31/232; A61K 31/685; A61K 31/688; A61K 31/7032; A61K 31/7034; A61K 47/34; A01K 27/001; A01K 27/007; A61P 17/00; A61P 17/04; C08L 75/04; C08L 2203/02
See application file for complete search history.

(56) References Cited

U.S. PATENT DOCUMENTS

| | | | | |
|---|---|---|---|---|
| 4,543,247 A | * | 9/1985 | von Bittera | .......... A01K 27/007 |
| | | | | 119/654 |
| 7,759,325 B2 | * | 7/2010 | Dupont | ................ A61K 31/685 |
| | | | | 514/78 |
| 2018/0140638 A1 | * | 5/2018 | Escaich Ferrer | ...... A61K 35/30 |

FOREIGN PATENT DOCUMENTS

| | | |
|---|---|---|
| GB | 2114442 A | 8/1983 |
| GB | 2316871 A | 3/1998 |
| JP | S57-096650 A | 6/1982 |
| JP | H04-290820 A | 10/1992 |
| JP | 2004036067 A | 2/2004 |

OTHER PUBLICATIONS

EMA Adjuvant. Obtained online on Jun. 20, 2024 from Wayback Machine <https://web.archive.org/web/20181002144048/https://www.ema.europa.eu/en/glossary/adjuvant>. (Year: 2018).*
Hunter et al. Obtained online on Jun. 20, 2024 from <https://web.archive.org/web/20190811031703/https://vcahospitals.com/know-your-pet/allergy-flea-allergy-dermatitis-in-dogs>. (Year: 2019).*
Worman et al. Biochemistry, 1986, 25, 1549-1555. (Year: 1986).*
Medicine. Merriam-Webster definition obtained online on Jun. 22, 2024 from Wayback Machine <https://web.archive.org/web/20130123100643/https://www.merriam-webster.com/dictionary/medicine>. (Year: 2013).*
Gottlieb, R. A.; Babior, B. M. "Regulation of Fas-Mediated Apoptosis." Current Topics in Cellular Regulation, vol. 35, Academic Press, 1997, pp. 69-105. (Year: 1997).*
Virbac. "Flea Infestation," available online Aug. 11, 2020, accessed on Webarchive.org on Jun. 4, 2025. https://web.archive.org/web/20200811011808/https://ph.virbac.com/home/every-disease-1/flea-allergy-dermatitis.html. (Year: 2020).*
Cerrato, S. et al. "Effects of sphingolipid extracts on the morphological structure and lipid profile in an in vitro model of canine skin," The Veterinary Journal, 2016, vol. 212, pp. 58-64. (Year: 2016).*
Marsella Rosanna et al., "Topical Treatment with Sphingolipids and Glycosaminoglycans for Canine Atopic Dermatitis", Journal, 2020, 1-10, vol. 16, No. 1, BMC Veterinary Research.
Blaskovic et al., "The Effect of a Spot-On Formulation Containing Polyunsaturated Fatty Acids and Essential Oils on Dogs with Atopic Dermatitis", Journal, 2014, 39-43, vol. 199, The Veterinary Journal.
Rosanna Marsella, "Atopic Dermatitis in Domestic Animals: What Our Current Understanding Is and How This Applies to Clinical Practice", Article, 2021, 1-18, vol. 8, No. 124, Veterinary Sciences.

* cited by examiner

*Primary Examiner* — Sue X Liu
(74) *Attorney, Agent, or Firm* — Hayes Soloway PC

(57) ABSTRACT

The present invention relates to a collar for non-human animals, preferably for companion animals, comprising a polymeric matrix and a lipid extract comprising sphingomyelins. It also refers to the collar for use as a medicine, particularly for use as an adjuvant and for use in the treatment or prevention of atopic dermatitis or allergic dermatitis, as well as in restoring the integrity of the skin during or after an atopic dermatitis or an allergic dermatitis, increasing the hydration and flexibility of the skin, facilitating skin regeneration or reducing itching of the skin.

6 Claims, 4 Drawing Sheets

DERMATOLOGICAL COLLAR FOR NON-HUMAN ANIMALS

CROSS-REFERENCE TO RELATED APPLICATIONS AND PRIORITY

This patent application claims priority from European Patent Application No. 21382717.3 filed Jul. 30, 2021. This patent application is herein incorporated by reference in its entirety.

TECHNICAL FIELD

The present invention relates to a collar for non-human animals, incorporating a lipid extract comprising sphingomyelins. It also refers to the collar for use as a medicine, particularly for use as an adjuvant and for use in the treatment or prevention of atopic dermatitis or allergic dermatitis, as well as in restoring the integrity of the skin during or after atopic dermatitis or allergic dermatitis, increasing the hydration and flexibility of the skin, facilitating skin regeneration or reducing itching of the skin.

STATE OF THE ART

Atopic dermatitis is a chronic inflammatory dermatosis characterised by itchy and scaly rashes. It is a multifactorial disease that results from the interaction of genetic factors, defects in the barrier function, environmental factors, susceptibility to skin infections and a number of immunological factors.

Atopic dermatitis is a fairly common disease in companion animals. The fact that there is a racial predisposition in dogs makes us suspect the great importance of genetic factors. The most common sign in dogs is the presence of itching of the skin as a result of constant scratching, licking or rubbing.

Steroids, antihistamines or antibiotics are commonly prescribed to treat atopic dermatitis. If these drugs are used for a long period of time, some unwanted side effects may occur. That is why there is a need to find alternative treatments, as well as routes of administration of the same that are effective and that, moreover, are comfortable for both the companion animal and for the person administering the treatment.

The topical route is used in the treatment of atopic dermatitis in companion animals, and this type of administration includes the administration of topical solutions in pipettes (spot-on solution).

M. Blaskovic et al. (*Vet. J.* 199, 39-43 (2014)) describe the use of a spot-on formulation, containing polyunsaturated fatty acids and essential oils, on dogs with atopic dermatitis. The product is administered once a week for eight weeks.

R. Marsella et al. (*BMC Vet. Res.* 16, 92 (2020)) describe the use of the Atopivet Spot-on product on dogs with atopic dermatitis. This product, as a topical solution in pipettes, contains sphingolipids and glycosaminoglycans. The content of a pipette is administered twice a week, for eight weeks, on the withers and the back of the pet, as well as on the areas where the lesions are located.

The need to use 8 or 16 pipettes during the spot-on treatment makes the product more expensive. It is also important to highlight the inconvenience that having to apply the product so frequently and on the various affected areas of the pet's body entails for both the dog and the owner.

Therefore, an alternative topical route to spot-on pipettes is required for administering an active substance for atopic dermatitis that is effective, easy to apply, cost-effective, and which releases the active substance over time, without needing to be regularly applied every week.

Collars for companion animals are widely used to topically administer antiparasitic treatments (see, for example, patent GB2316871B); however, to date, its use in administering an active substance for atopic dermatitis has not been described.

It is not apparent that, even if a pesticide collar is effective, one that contains an active substance for atopic dermatitis will be effective. It should not be ruled out that problems may occur such as the insufficient release of the active substance from the collar and/or the scant distribution of the same over the animal's entire body until reaching the areas of the lesions.

DESCRIPTION OF THE INVENTION

The present inventors have found that the collar of the present invention, defined below, is novel, it shows an adequate in vitro kinetic release pattern of the lipid extract in a fatty medium, it leads to a significant decrease, at four and eight weeks, in the lesions caused by atopic dermatitis in non-human animals, preferably in companion animals, and it significantly reduces itching of the skin, at four and eight weeks. To that end, it can be used in the treatment or prevention of atopic dermatitis or allergic dermatitis, as well as in restoring the integrity of the skin during or after atopic dermatitis or allergic dermatitis, increasing the hydration and flexibility of the skin, reducing itching of the skin or facilitating skin regeneration in a non-human animal, preferably a companion animal.

Accordingly, the present invention relates to a collar for non-human animals, preferably companion animals, comprising a polymeric matrix and a lipid extract, wherein the lipid extract comprises sphingomyelins.

In a preferred embodiment, the invention relates to the previously defined collar, wherein the lipid extract is suitable to be released onto the body of the non-human animal, preferably of the companion animal.

In another preferred embodiment, the invention relates to the previously defined collar, wherein the polymeric matrix is thermoplastic polyurethane, also known as TPU.

In another preferred embodiment, the invention relates to the previously defined collar, wherein the lipid extract comprises at least 30% by weight of sphingomyelins with respect to the total weight of the lipid extract.

In another preferred embodiment, the invention relates to the previously defined collar, wherein the lipid extract comprises at least 45% by weight of sphingomyelins with respect to the total weight of the lipid extract, more preferably it comprises at least 50% by weight of sphingomyelins with respect to the total weight of the lipid extract.

In another preferred embodiment, the invention relates to the previously defined collar, wherein the lipid extract comprises between 30% and 70% by weight of sphingomyelins with respect to the total weight of the lipid extract, between 1% and 15% by weight of ceramides with respect to the total weight of the lipid extract, less than 0.5% by weight of sulphatides with respect to the total weight of the lipid extract, less than 0.5% by weight of gangliosides with respect to the total weight of the lipid extract, between 20% and 58% by weight of phospholipids with respect to the total weight of the lipid extract, and between 0.5% and 10% by weight of neutral lipids with respect to the total weight of the lipid extract, and the sum of the percentages of the lipid extract components is equal to 100%.

In a more preferred embodiment, the invention relates to the previously defined collar, wherein the lipid extract comprises between 45% and 65% by weight of sphingomyelins with respect to the total weight of the lipid extract, between 2% and 6% by weight of ceramides with respect to the total weight of the lipid extract, less than 0.2% by weight of sulphatides with respect to the total weight of the lipid extract, less than 0.2% by weight of gangliosides with respect to the total weight of the lipid extract, between 25% and 45% by weight of phospholipids with respect to the total weight of the lipid extract, and between 0.5% and 4.5% by weight of neutral lipids with respect to the total weight of the lipid extract, and the sum of the percentages of the lipid extract components is equal to 100%.

In another preferred embodiment, the invention relates to the previously defined collar, wherein the lipid extract comprises between 50% and 59% by weight of sphingomyelins with respect to the total weight of the lipid extract, between 3.5% and 5.2% by weight of ceramides with respect to the total weight of the lipid extract, less than 0.05% by weight of sulphatides with respect to the total weight of the lipid extract, less than 0.05% by weight of gangliosides with respect to the total weight of the lipid extract, between 32% and 44% by weight of phospholipids with respect to the total weight of the lipid extract, and between 1% and 3% by weight of neutral lipids with respect to the total weight of the lipid extract, and the sum of the percentages of the lipid extract components is equal to 100%.

Within the group of sphingomyelins, dihydrosphingomyelins are also included. The group of ceramides includes ceramides, dihydroceramides, glucosylceramides, and lactosylceramides. The phospholipids include, for example, phosphatidylcholines, lysophosphatidylcholines, lysophosphatidylethanolamines, lysophosphatidylserines, phosphatidylcholine plasmalogens and lysophosphatidylethanolamine plasmalogens. The neutral lipids include, for example, diacylglycerols and triacylglycerols. The lipid extract contains a very low content of sulphatides, which is usually less than 0.5%, preferably less than 0.05%, and more preferably less than 0.01%. It also contains a very low content of gangliosides (GM1, GM2, GM3 and GD1), which is usually less than 0.5%, preferably less than 0.05%, and more preferably less than 0.01%. In fact, although the method of determining sulphatides and gangliosides used makes it possible to detect 0.006 mg/g of sulphatides and 0.009 mg/g of gangliosides, in the three batches of lipid extract, defined below and used in the present invention, no amount of sulphatides and gangliosides was detected.

In another preferred embodiment, the invention relates to the previously defined collar, wherein the lipid extract is of animal origin, preferably bovine or porcine, more preferably from porcine intestinal mucosa or from bovine or porcine trachea, and even more preferably the lipid extract is from bovine trachea.

In another preferred embodiment, the invention relates to the previously defined collar, wherein the collar comprises from 2% to 5% by weight of the lipid extract with respect to the weight of the collar, preferably comprises from 2% to 3% by weight of the lipid extract with respect to the weight of the collar, and more preferably comprises 2.5% by weight of the lipid extract with respect to the weight of the collar.

In another preferred embodiment, the invention relates to the previously defined collar, wherein the polymeric matrix and the lipid extract are present in the collar in a weight ratio of polymeric matrix to lipid extract comprised between 30:1 and 29:1, more preferably the ratio is 29.8:1 or 29.5:1.

In another preferred embodiment, the invention relates to the previously defined collar, wherein the collar is a dermatological collar.

The present invention also relates to a method for preparing the collar, previously defined, comprising the following steps:

1) heating the polymeric matrix;
2) adding to the polymeric matrix of step 1) a mixture comprising a plasticizer and a stabilizer;
3) cooling the mixture of step 2);
4) adding the lipid extract, and
5) moulding the mixture resulting from step 4) into a collar shape.

In another embodiment, the invention relates to the method for preparing the previously defined collar, wherein the polymeric matrix is thermoplastic polyurethane (TPU), and it is preferably heated to a temperature between 90° C. and 95° C.

In another embodiment, the invention relates to the method for preparing the previously defined collar, wherein the plasticizer is ethylhexyl diphenyl phosphate and the stabilizer is a mixture of C7-9-alkyl 3-(3,5-di-trans-butyl-4-hydroxyphenyl)propionate, isomers of 2-(2H-benzotriazol-2-yl)-4-methyl-(n)-dodecylphenol, bis(1,2,2,6,6-pentamethyl-4-piperidyl) sebacate and methyl 1,2,2,6,6-pentamethyl-4-piperidyl sebacate.

In another embodiment, the invention relates to the method for obtaining the previously defined collar, wherein in step 2) a perfume is added, and preferably wherein the perfume is lavender oil.

In another embodiment, the invention relates to the method for obtaining the previously defined collar, wherein in step 3) the mixture of step 2) is cooled to room temperature.

In another embodiment, the invention relates to the method for obtaining the previously defined collar, wherein steps 1), 2), 3) and 4) are carried out under stirring.

In another embodiment, the invention relates to the method for obtaining the previously defined collar, wherein the mixture resulting from step 4) is injection moulded into a collar shape. Collars of different lengths can be obtained, for example, measuring 35 cm or 75 cm.

In another embodiment, the invention relates to the method for obtaining the previously defined collar, wherein in step 4 a dye is added, such as black iron oxide.

In another embodiment, the invention relates to the method for obtaining the previously defined collar, wherein the polymeric matrix and the lipid extract are present in the collar in a weight ratio of polymeric matrix to lipid extract comprised between 30:1 and 29:1, and more preferably the ratio is 29.8:1 or 29.5:1.

The present invention also relates to the previously defined collar for use as a medicine.

The present invention also relates to the previously defined collar for use as an animal health product.

When the collar of the invention is used as an animal health product, it will be understood that the collar is intended for the diagnosis, prevention, treatment, relief or cure of diseases or ailments of non-human animals.

The present invention also relates to the previously defined collar for use as an adjuvant.

When the collar of the invention is used as an adjuvant, it will be understood that the collar comprising the lipid extract complements or enhances the action of a main drug.

The present invention also relates to the previously defined collar, for use in the treatment or prevention of atopic dermatitis or allergic dermatitis in a non-human animal, preferably a companion animal.

Likewise, the present invention also relates to the use of a collar, previously defined, for the manufacture of a medicine for the treatment or prevention of atopic dermatitis or allergic dermatitis in a non-human animal, preferably in a companion animal.

Likewise, the present invention also relates to a method of treating or preventing atopic dermatitis or allergic dermatitis in a non-human animal, preferably in a companion animal, which comprises putting on a collar, previously defined, on the animal's neck.

The present invention also relates to a collar, previously defined, for use in restoring the integrity of the skin during or after atopic dermatitis or allergic dermatitis, increasing the hydration and flexibility of the skin, reducing itching of the skin or facilitating skin regeneration in a non-human animal, preferably in a companion animal.

Likewise, the present invention also relates to the use of the collar, previously defined, to restore the integrity of the skin during or after atopic dermatitis or allergic dermatitis, increasing the hydration and flexibility of the skin, reducing itching of the skin or facilitating skin regeneration in a non-human animal, preferably in a companion animal.

Likewise, the present invention also relates to a method for restoring the integrity of the skin during or after atopic dermatitis or allergic dermatitis, increasing the hydration and flexibility of the skin, reducing itching of the skin or facilitating skin regeneration in a non-human animal, preferably in a companion animal, which comprises putting on a collar, previously defined, on the animal's neck.

In another embodiment, the invention relates to the collar for any of the previously defined uses, characterised in that the collar is kept on the animal's neck for eight weeks so that the lipid extract is released onto the body of the non-human animal.

Throughout the present invention the term "animal" refers to a "non-human animal", preferably a "companion animal". Examples include, among others, a dog and a cat. Preferably, the animal to which the invention relates is a dog.

The present invention also relates to an animal health product in the form of the collar, previously defined.

The lipid extract of the collar of the present invention can be obtained by extractive methods from mammalian tissues, such as, for example, from porcine intestinal mucosa or bovine or porcine trachea. Preferably, it can be obtained from bovine trachea, which, once crushed, are subjected to enzymatic digestion in an aqueous medium (with proteolytic enzyme, preferably a subtilisin), at a temperature comprised, preferably, between 50° C. and 60° C., leaving a solid residue and an emulsion. Subsequently, it is decanted at a temperature, preferably, between 80° C. and 90° C., the solid residue is discarded, and the process continues with the emulsion, from which water is removed by vacuum evaporation. Next, the concentrate resulting from evaporation is resuspended in acetone, preferably at a temperature of 30° C., diatomaceous earth is added, it is filtered, and the insoluble fraction is resuspended in alcohol, preferably in methanol, at a temperature of 50° C. Next, it is filtered, the solid fraction is discarded, and the process continues with the liquid fraction. Subsequently, the methanol is partially eliminated from the liquid fraction until a concentrate is obtained, which, next, is precipitated with acetone. After decanting and eliminating the liquid fraction, the solid fraction obtained, if desired, can be washed several times with acetone, discarding the supernatant after each wash and keeping the solid fraction, which is then vacuum dried. Next, it can be ground and sieved. This solid fraction constitutes the lipid extract comprising sphingomyelins, used in the collar of the present invention. By following this method, various batches of lipid extract can be obtained, which can vary from one to another in the composition thereof (see, for example, in Table 1, the composition of three batches expressed as % by weight of each component with respect to the total weight of the lipid extract, the sum of the percentages of the lipid extract components being equal to 100%).

TABLE 1

| Component | Batch 1 | Batch 2 | Batch 3 |
|---|---|---|---|
| Sphingomyelins | 55.2 | 55.3 | 56.1 |
| Ceramides | 4.2 | 4.4 | 4.5 |
| Sulphatides | 0 | 0 | 0 |
| Gangliosides | 0 | 0 | 0 |
| Phospholipids | 38.2 | 37.8 | 37.3 |
| Neutral lipids | 2.4 | 2.5 | 2.1 |
| Total | 100.0 | 100.0 | 100.0 |

Taking into account the variability in the composition of different batches, the lipid extract obtained contains the groups of compounds shown in Table 2.

TABLE 2

| Component | % |
|---|---|
| Sphingomyelins | 30-70 |
| Ceramides | 1-15 |
| Sulphatides | <0.5 |
| Gangliosides | <0.5 |
| Phospholipids | 20-58 |
| Neutral lipids | 0.5-10 |

Preferably, the lipid extract obtained contains the groups of compounds shown in Table 3.

TABLE 3

| Component | % |
|---|---|
| Sphingomyelins | 45-65 |
| Ceramides | 2-6 |
| Sulphatides | <0.2 |
| Gangliosides | <0.2 |
| Phospholipids | 25-45 |
| Neutral lipids | 0.5-4.5 |

More preferably, the lipid extract obtained contains the groups of compounds shown in Table 4.

TABLE 4

| Component | % |
|---|---|
| Sphingomyelins | 50-59 |
| Ceramides | 3.5-5.2 |
| Sulphatides | <0.05 |
| Gangliosides | <0.05 |
| Phospholipids | 32-44 |
| Neutral lipids | 1-3 |

It should be noted that the lipid extract used in the present invention contains sphingomyelins and it contains practically no sulphatides or gangliosides. For example, in the three batches of lipid extract in Table 1, no amount of sulphatides and gangliosides was detected.

The Collar has, Among Others, the Following Advantages:

It allows for an effective release in time of the lipid extract in a fatty medium (which would be equivalent to the sebum from the skin of a companion animal), as can be seen in the in vitro study with release at 8, 15 and 22 days (see Example 3).

It shows efficacy in dogs with atopic dermatitis, producing a significant reduction (p<0.05) in lesions and itching, at four and eight weeks (see Example 4).

At mid-treatment (4 weeks) it already shows very good efficacy, both in reducing lesions and reducing itching. Indeed, a significant decrease from 0 to 4 weeks was observed in the CADESI (*Canine Atopic Dermatitis Extent and Severity Index*) (lesions) (43%; p<0.05) and a significant decrease from 0 to 4 weeks was observed in the PICAD (*Pruritus Index for Canine Atopic Dermatitis*) (itching) (52.3%; p<0.05). The significant decrease (p<0.05) was observed from 0 to 2 weeks (25.8%) and from 1 to 2 weeks (20.6%) even in the PVAS index (itching). On the contrary, with the Atopivet Spot-on pipettes (R. Marsella et al., *BMC Vet. Res.* 16, 92 (2020)) the decrease in the CADESI was only 5.1% at 4 weeks and it was not statistically significant; as for the PVAS index, no effect was seen at 4 weeks. Therefore, the collar acts earlier on atopic dermatitis than Atopivet Spot-on.

It is not necessary to combine the lipid extract with glycosaminoglycans for the collar to be effective, whereas in the Atopivet Spot-on pipettes, the sphingolipids must be combined with glycosaminoglycans.

Administering the treatment is easy and comfortable. It only requires fitting the collar on the neck of the companion animal and removing it after two months. With Spot-on pipettes, creams or gels, it is necessary to look for lesions every time and apply the solution from the pipettes, the cream or the gel on them.

The frequency of administration of the product is reduced. The collar is placed once every two months, whereas, for example, Spot-on pipettes are applied once a week for eight weeks, or twice a week for eight weeks, as in the case of Atopivet Spot-on pipettes (a total of sixteen applications).

It is more cost-effective than Spot-on pipettes, which results in a lower cost for the companion animal's caregiver. For example, compared to Atopivet Spot-on pipettes, monthly savings are approximately 50%.

The pet does not need any special care before or after putting on the collar, whereas with Spot-on pipettes it is advisable to wash the pet before each application and not immediately after applying the pipette, so as not to remove the product from the skin.

Throughout the description and the claims, the word "comprises" and its variants do not intend to exclude other technical features, additives, components or steps. Thus, the term "comprises" should be understood to also include the case of "consists solely of" and that of "consists essentially of".

For those skilled in the art, other objects, advantages, and features of the invention may be partially deduced from both the description and the embodiment of the invention. The following examples and figures are provided by way of illustration and are not intended to limit the present invention.

EXAMPLES

Figure 1:
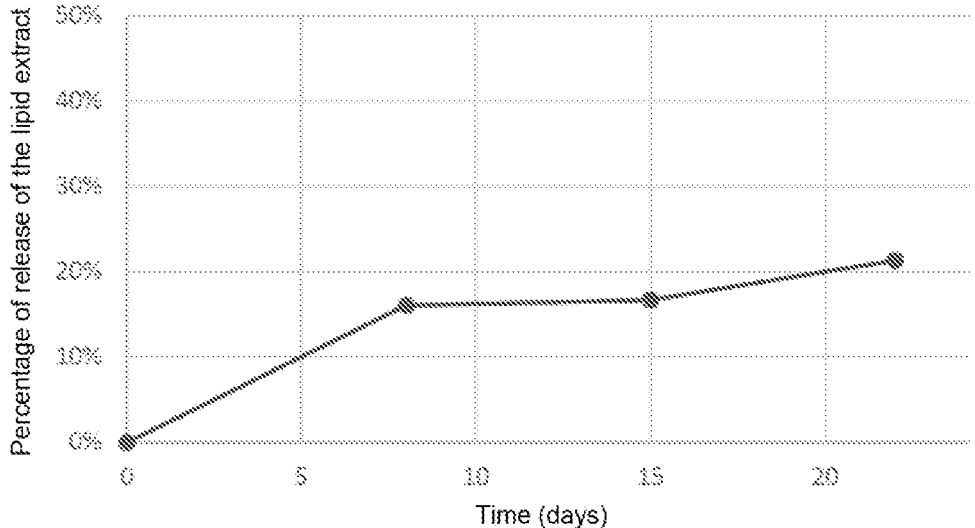
FIG. 1 shows the percentage of release of the lipid extract over time, in days, in an in vitro study.

The following examples are for illustrative purposes and do not represent a limitation on the scope of the present invention.

Example 1: Preparation of a 35 cm Long Collar 9.76 g of thermoplastic polyurethane (TPU) were introduced in a reactor preheated to a temperature of 90° C.-95° C. and under stirring. Once the polymer reached said temperature, 2.62 g of the ethylhexyl diphenyl phosphate plasticizer, 0.0655 g of a mixture of the stabilizers C7-9-alkyl 3-(3,5-di-trans-butyl-4-hydroxyphenyl)propionate, isomers of 2-(2H-benzotriazol-2-yl)-4-methyl-(n)-dodecylphenol, bis(1,2,2,6,6-pentamethyl-4-piperidyl) sebacate and methyl 1,2,2,6,6-pentamethyl-4-piperidyl sebacate and 0.1965 g of lavender oil were gradually added. Stirring was continued until said mixture was completely incorporated into the polymer. Next, the resulting mixture was cooled to room temperature, maintaining stirring at all times. Subsequently, 0.33 g of lipid extract were added (see composition in Table 4), and the resulting mixture was stained (with black iron oxide) and homogenised. The reactor was drained and finally the mixture obtained was shaped in a mould by injection. The collar obtained contained 2.5% lipid extract by weight with respect to the weight of the collar.

Example 2: Preparation of a 75 cm Long Collar

The same methodology explained for the 35 cm collar was repeated, but in this case 19.67 g of thermoplastic polyurethane, 0.66 g of lipid extract, 5.28 g of the ethylhexyl diphenyl phosphate plasticizer, 0.132 g of a mixture of the stabilizers C7-9-alkyl 3-(3,5-di-trans-butyl-4-hydroxyphenyl)propionate, isomers of 2-(2H-benzotriazol-2-yl)-4-methyl-(n)-dodecylphenol, bis(1,2,2,6,6-pentamethyl-4-piperidyl) sebacate and methyl 1,2,2,6,6-pentamethyl-4-piperidyl sebacate and 0.396 g of lavender oil were used. The collar obtained contained 2.5% lipid extract by weight with respect to the weight of the collar.

Example 3: In Vitro Study of the Release of the Lipid Extract

The purpose of this study was to evaluate in vitro how much and for how long the lipid extract was released from the collar in a fatty medium, considered representative of the sebum from the skin of domestic animals.

Materials and Methods

This study was conducted with a laboratory batch of three collars, obtained according to Example 1, containing 2.5% by weight of lipid extract.

The three collars were fragmented, and the pieces of each collar were immersed in a fatty medium consisting of a mixture of triglycerides and shaken with a magnetic stirrer. A piece of each collar was taken at each moment to be analysed: at the beginning, and after 8, 15 and 22 days. At each of these points in time, the same laboratory analysis method was carried out: quantification of methyl palmitate (component of the lipid extract) by gas chromatography. This made it possible to determine the remaining content of lipid extract in each of the three collars, and then calculate the average of the three collars. The percentage of release was determined with this value.

Results

The results obtained are summarised in Table 5 below:

TABLE 5

| | RESULTS | |
|---|---|---|
| Time (days) | Percentage of lipid extract remaining in the collar (average of three collars) | Percentage of release of the lipid extract (average of three collars) |
| 0 | 2.56 | 0 |
| 8 | 2.15 | 16 |
| 15 | 2.13 | 17 |
| 22 | 2.01 | 21 |

FIG. 1 also shows the percentage of release of the lipid extract over time.

As can be observed, at 22 days, the percentage of release of the lipid extract was 21% in the mixture of triglycerides. Thus, the study showed good release kinetics of the lipid extract in a fatty medium.

Example 4: In Vivo Study of Efficacy and Safety in Dogs with Atopic Dermatitis The purpose of this study was to determine the effects of the application of the collar in the management of canine patients with atopic dermatitis, assessing the safety of the application of the product and the effects on the extent and severity of the lesions, as well as on itching.

Materials and Methods

This study included 12 dogs of different breeds, gender and ages with a confirmed diagnosis of non-seasonal atopic dermatitis and without other significant concomitant diseases, to which the collar of Example 1 or of Example 2 was fitted on the neck, depending on the size of the dog.

The total duration of treatment and follow-up from the start of treatment was 8 weeks. Veterinarian control visits were conducted at the start of treatment (0 weeks) and then at 4 and 8 weeks using 2 scores (*Canine Atopic Dermatitis Extent and Severity Index*—CADESI)-4; and *Pruritus Index for Canine Atopic Dermatitis*—PICAD), in addition to weekly evaluations of itching performed by the owner (*Pruritus Visual Analog Scale*—PVAS).

The CADESI made it possible to score various lesions (erythema, lichenification, and alopecia/excoriation) on different body regions (pinna, armpits, front and hind legs, elbow folds, carpal and metacarpal pads, flanks, inguinal regions, abdomen, perineal region and proximal ventral portion of the tail).

The PICAD made it possible to score itching on various body regions, observing the frequency and intensity of: scratching/shaking the ears, scratching/rubbing the head, scratching/rubbing/licking the trunk or armpits, scratching/rubbing/licking the ventral abdomen, licking/biting the front feet, licking/biting the hind feet, licking/biting the legs and rubbing/licking/biting the anogenital region.

The PVAS index made it possible to score the itching observed by the dog's owner, who noted the degree of itching shown by the pet once a week, on a scale from 0 to 10, where 0 was no itching and 10 was unbearable itching.

Results:

The application of the collar for 8 weeks was found to be safe and did not lead to the appearance of associated side effects.

Figure 2:
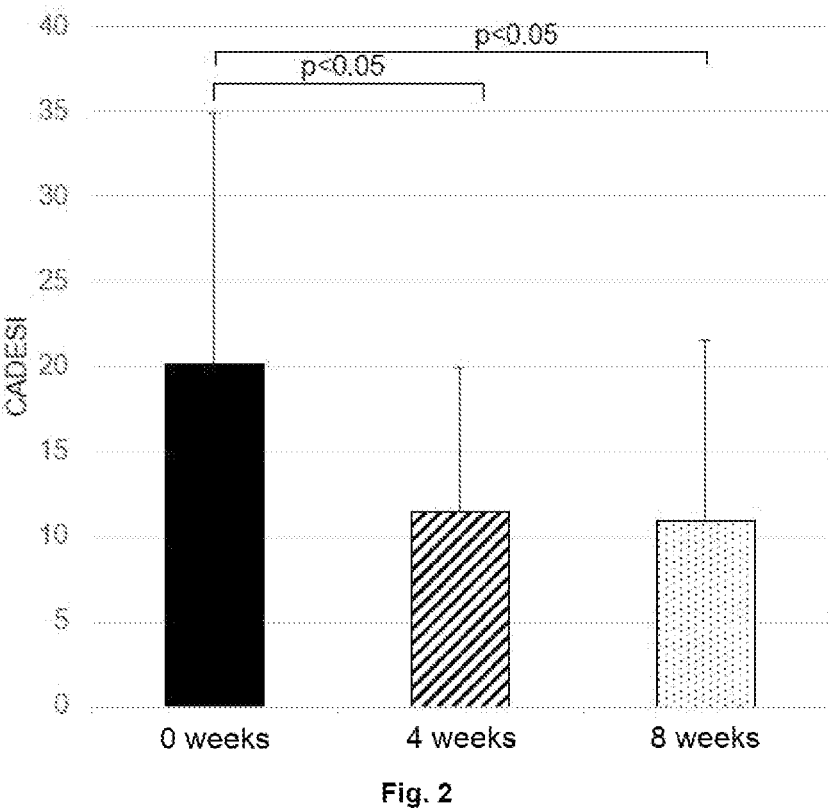
FIG. 2 shows the mean score of the lesions using the CADESI, at the beginning, and at four and eight weeks of treatment.

A significant decrease from 0 to 4 weeks (43%; $p<0.05$), in addition to a significant decrease from 0 to 8 weeks (48.6%; $p<0.05$) was observed in the CADESI (see FIG. 2).

Figure 3:
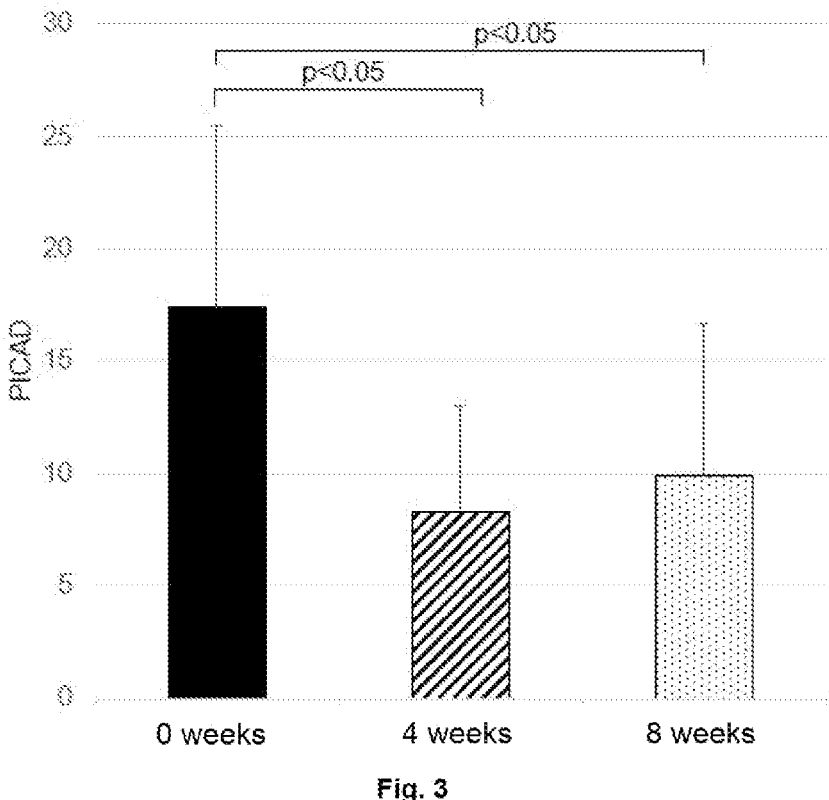
FIG. 3 shows the mean score of the degree of itching using the PICAD, at the beginning, and at four and eight weeks of treatment.

A significant decrease from 0 to 4 weeks (52.3%; $p<0.05$), and a significant decrease from 0 to 8 weeks (43.2%; $p<0.05$) was observed in the PICAD (see FIG. 3).

Figure 4:
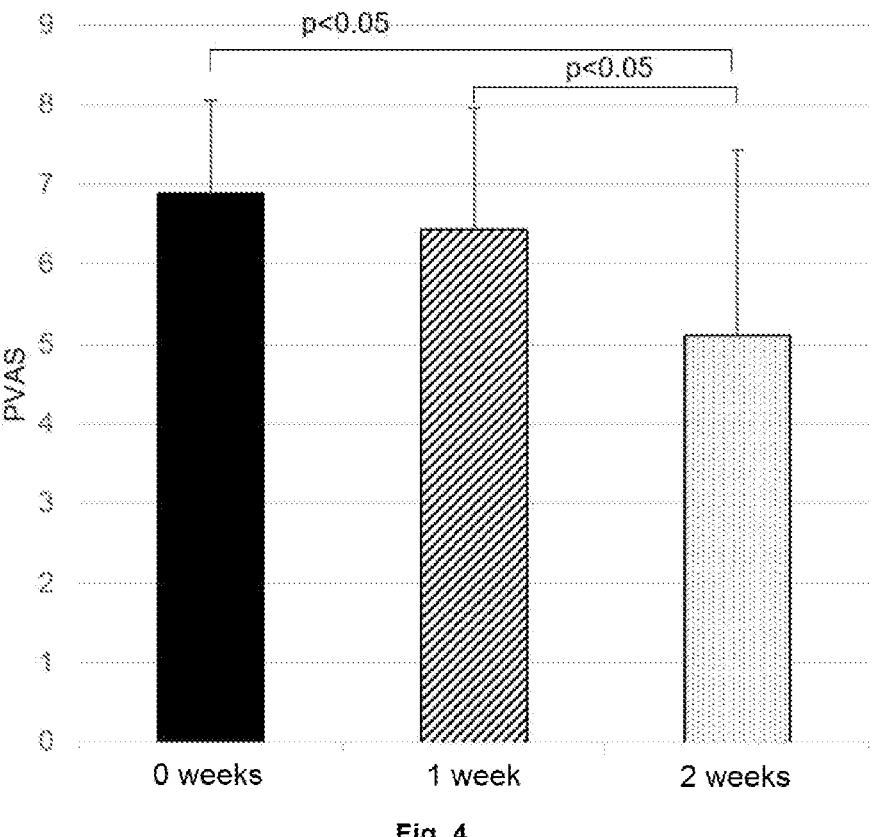
FIG. 4 shows the mean score of the degree of itching by the owner of the dog using the PVAS index, at the beginning, and at one week and two weeks of treatment.

A significant decrease ($p<0.05$) from 0 to 2 weeks (25.8%) and from 1 to 2 weeks (20.6%) was observed in the PVAS index (see FIG. 4).

The invention claimed is:

1. A collar for canines comprising:

a polymeric matrix and a lipid extract, wherein the lipid extract consisting of between 50% and 59% by weight of sphingomyelins with respect to the total weight of the lipid extract, between 3.5% and 5.2% by weight of ceramides with respect to the total weight of the lipid extract, less than 0.05% by weight of sulphatides with respect to the total weight of the lipid extract, less than 0.05% by weight of gangliosides with respect to the total weight of the lipid extract, between 32% and 44% by weight of additional phospholipids with respect to the total weight of the lipid extract, and between 1% and 3% by weight of additional neutral lipids with respect to the total weight of the lipid extract, and the sum of the percentages of the lipid extract components is equal to 100%; and wherein the collar is configured to release at least 20% of the lipid extract within at least 20 days from being attached to the canine.

2. The collar according to claim 1, wherein the polymeric matrix is thermoplastic polyurethane.

3. The collar according to claim 1, wherein the lipid extract is bovine or porcine.

4. The collar according to claim 3, wherein the lipid extract is from bovine or porcine trachea.

5. The collar according to claim 1, comprising from 2% to 5% by weight of the lipid extract with respect to the weight of the collar.

6. The collar according to claim 5, comprising 2.5% by weight of the lipid extract with respect to the weight of the collar.

* * * * *